US 7,345,082 B2

(12) United States Patent
Hilpert et al.

(10) Patent No.: US 7,345,082 B2
(45) Date of Patent: Mar. 18, 2008

(54) PHOSPHINIC ACIDS

(75) Inventors: Hans Hilpert, Muenchenstein (CH);
Roland Humm, Freiburg (DE);
Dietmar Knopp, Basel (CH); Peter Weiss, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 404 days.

(21) Appl. No.: 10/983,363

(22) Filed: Nov. 8, 2004

(65) Prior Publication Data

US 2005/0107341 A1    May 19, 2005

(30) Foreign Application Priority Data

Nov. 11, 2003   (EP)   ............................ 03025852

(51) Int. Cl.
*A61K 31/405*   (2006.01)
*C07F 9/02*   (2006.01)

(52) U.S. Cl. ................... 514/415; 514/79; 514/80; 514/424; 514/429; 548/413; 558/169; 546/22

(58) Field of Classification Search ............... 548/413; 558/169; 546/22; 514/79, 80, 415, 424, 514/429

See application file for complete search history.

(56) References Cited

U.S. PATENT DOCUMENTS 6,630,501 B1   10/2003   Dive et al.

FOREIGN PATENT DOCUMENTS

| WO | WO 03/040096 | 5/2003 |
|---|---|---|
| WO | WO 03/045913 | 6/2003 |
| WO | WO 03/072535 | 9/2003 |

OTHER PUBLICATIONS

Lloyd et al., 1996, CAS: 125:196335.*
Or Vincent et al., 1997, CAS: 127:117584.*
Taylor W. G. et al., J. Agricultural & Food Chemistry, vol. 38 pp. 1422-1427 (1990).
Liu, X. et al., J. Organomet. Chem. vol. 646, pp. 212-222 (2002).
Sampson, N. S. et al., Biochemistry, vol. 30 pp. 2255-2263 (1991).
Baylis, E. K. et al., J. Chem. Soc. Perkin. Trans. vol. 1 pp. 2845-2853 (1984).
Dijols, S. et al., Biochemistry vol. 41, pp. 9286-9292 (2002).
Jacobs R. T. et al., J. Med. Chem. vol. 37, pp. 1282-1297 (1994).
Bailey, K. et al., Can. J. of Chem. vol. 49, pp. 3143-3151 (1971).
Vassiliou S. et al., Phosphinic pseudo-tripeptides as potent inhibitors of matrix metalloproteinases: a structure-activity study, Journal of Medicinal Chemistry, American Chemical Society, Washington, US, vol. 42, No. 14, pp. 2610-2620, (1999), XP002135494.
Yiotakis et al., Protection of the Hydroxyphosphinyl Function of Phosphinic Dipeptides by Adamantyl. Application to the Solid-Phase Synthesis of Phosphinic Peptides, Journal of Organic Chemistry, American Chemical Society, Easton, US, vol. 61, No. 1, pp. 6601-6605 (1996), XP002165430, p. 6605, col. 2, peptide 9.
Jiracek J. et al, Development of the First Potent and Selective Inhibitor of the Zincendopeptidase Neurolysin Using a Systematic Approach Based on Combinatorial Chemistry of Phosphinic Peptides, Journal of Biological Chemistry, vol. 271, No. 32, pp. 19606-19611 (1996), XP000677097.
Vincent Bruno et al, Effect of a Novel Selective and Potent Phosphinic Peptide Inhibitor of Endopeptidase 3.4.24.16 on Neurotensin-Induced Analgesia and Neuronal Inactivation, British Journal of Pharmacology, vol. 121, No. 4, pp. 705-710 (1997), XP002316977.
Yiotakis Athanasios et al, Cyclic Peptides with a Phosphinic Bond as Potent Inhibitors of a Zinc Bacterial Collagenase, Journal of Medicinal Chemistry, vol. 37, No. 17, pp. 2713-2720 (1994), XP002316978, p. 2717, col. 2, line 34-line 36.
Grobelny D et al, Selective Phosphinate Transition-State Analogue Inhibitors of the Protease of Human Immunodeficiency Virus, Biochemical and Biophysical Research Communications, vol. 169, No. 3, pp. 1111-1116 (1990), XP009043775.

* cited by examiner

*Primary Examiner*—Rei-tsang Shiao
(74) *Attorney, Agent, or Firm*—George W. Johnston; Patricia S. Rocha-Tramaloni; Kimberly J. Prior

(57) ABSTRACT

The present invention relates to phosphinic acid derivatives of formula I $$R^1-\underset{O}{\overset{\|}{C}}-\underset{H}{N}-\underset{CH_2-R^2}{\overset{|}{CH}}-\underset{\underset{OH}{\overset{\|}{O}}}{P}-CH_2-\underset{R^3}{\overset{|}{CH}}-\underset{O}{\overset{\|}{C}}-\underset{H}{N}-R^4$$

wherein $R^1$, $R^2$, $R^3$ and $R^4$ are described hereinabove. These compounds can be used in the treatment or prevention of a disease related to the inhibition of β-secretase, inter alia for the treatment of Alzheimer's disease.

32 Claims, No Drawings

PHOSPHINIC ACIDS

FIELD OF THE INVENTION

The invention relates to β-secretase inhibitors and their use in the treatment of neurodegenerative diseases.

BACKGROUND OF THE INVENTION

Alzheimer's disease (AD) is the most common cause of dementia in later life. Pathologically AD is characterized by the deposition in the brain of amyloid in extracellular plaques and intracellular neurofibrillary tangles. The amyloid plaques are mainly composed of amyloid peptides (Abeta peptides) which originate from the β-Amyloid Precursor Protein (APP) by a series of proteolytic cleavage steps. Several forms of APP have been identified of which the most abundant are proteins of 695, 751 and 770 amino acids length. They all arise from a single gene through differential splicing. The Abeta peptides are derived from the same domain of the APP but differ at their N- and C-termini, the main species are of 40 and 42 amino-acid length.

Abeta peptides are produced from APP through the sequential action of 2 proteolytic enzymes termed β- and γ-secretase. β-Secretase cleaves first in the extracellular domain of APP just outside of the trans-membrane domain (TM) to produce a C-terminal fragment of APP containing the TM- and cytoplasmatic domain (CTFβ). CTFβ is the substrate for γ-secretase which cleaves at several adjacent positions within the TM to produce the Aβ peptides and the cytoplasmic fragment. The majority of Abeta peptides is of 40 amino acids length (Aβ40), aminor species carries 2 additional amino acids at its C-terminus. Latter is supposed to be the more pathogenic amyloid peptide.

The β-secretase is a typical aspartyl protease. The γ-secretase is a proteolytic activity consisting of several proteins, its exact composition is incompletely understood. However, the presenilins are essential components of this activity and may represent a new group of atypical aspartyl proteases which cleave within the TM of their substrates and which are themselves polytopic membrane proteins. Other essential components of γ-secretase may be nicastrin and the products of the alpha and pen-2 genes. Proven substrates for γ-secretase are the APP and the proteins of the Notch receptor family, however, γ-secretase has a loose substrate specificity and may cleave further membrane proteins unrelated to APP and Notch.

SUMMARY OF THE INVENTION

The invention relates to phosphinic acid derivatives, processes for their preparation, compositions containing said phosphinic acid derivatives and their use in the prevention and treatment of diseases.

More particularly, the present invention relates to compounds of formula I

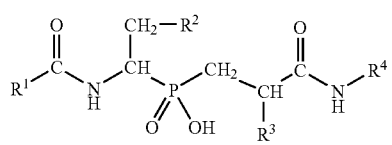

(I)

wherein
$R^1$ is aryl or heteroaryl;
$R^2$ is $(C_1-C_5)$-alkyl or phenyl;
$R^3$ is hydrogen, $(C_1-C_5)$-alkyl, O—$(C_1-C_5)$-alkyl or phenyl;
$R^4$ is $(C_1-C_6)$-alkyl, $(C_3-C_6)$-cycloalkyl, phenyl, pyridyl, or indolyl;

and to pharmaceutically acceptable salts thereof.

The invention also provides all forms of optically pure enantiomers or diastereomeric mixtures for compounds of formula I.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

The term "aryl" denotes a monovalent cyclic aromatic hydrocarbon radical consisting of one or more fused rings in which at least one ring is aromatic in nature. Examples for aryl include phenyl which may be unsubstituted or substituted by a substituent selected from OH, halogen, $(C_1-C_5)$-alkyl, O—$(C_1-C_5)$-alkyl, $N[(C_1-C_6)alkyl]_2$, $COO(C_1-C_5)$ alkyl, pyrrolidonyl and $C(O)NR^5R^6$, wherein $R^5$ is hydrogen or $(C_1-C_5)$-alkyl and $R^6$ is unsubstituted $(C_1-C_5)$-alkyl or $(C_1-C_5)$-alkyl substituted by phenyl.

The term "heteroaryl" denotes a monovalent aromatic carbocyclic radical. Examples for heteroaryl include indolyl, quinolinyl, isoquinolinyl and pyridyl. The hetero-aryl may be unsubstituted or substituted by $(C_1-C_5)$-alkyl.

As used herein, the term "alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Alkyl may be unsubstituted or substituted by a substituent selected from halogen, $N[(C_1-C_6)alkyl]_2$, $(C_3-C_6)$cycloalkyl, aryl, such as phenyl, COOH, $COOCH_3$, $S-(C_1-C_5)$-alkyl, and heteroaryl, such as isoxazolyl.

The term "cycloalkyl" denotes a saturated carbocyclic group, containing 3 to 7 carbon atoms. Examples include cyclopropyl, cyclobutyl, cyclopentyl and cyclohexyl.

Examples of halogen include fluorine, chlorine, iodine and bromine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids As pharmaceutically acceptable salts there may, e.g., be used the alkali metal or ammonium salts which can be prepared, e.g. by titration of the compounds with inorganic or organic bases, e.g., sodium or potassium hydrogen carbonates, aqueous solutions of sodium or potassium hydroxide or aqueous solutions of ammonia or of amines, e.g. trimethylamine or triethylamine.

The term "therapeutically effective amount" means an amount that is effective to prevent, alleviate or ameliorate symptoms of disease or prolong the survival of the subject being treated.

The present invention relates to compounds of formula I

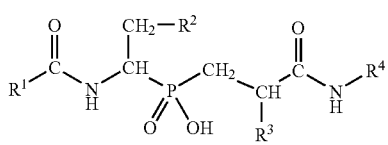
(I)

wherein
R$^1$ is aryl or heteroaryl;
R$^2$ is (C$_1$-C$_5$)-alkyl or phenyl;
R$^3$ is hydrogen, (C$_1$-C$_5$)-alkyl, O—(C$_1$-C$_5$)-alkyl or phenyl;
R$^4$ is (C$_1$-C$_6$)-alkyl, (C$_3$-C$_6$)-cycloalkyl, phenyl, pyridyl, or indolyl; and to pharmaceutically acceptable salts thereof.

In one embodiment the present invention provides a compound of formula I wherein R$^1$ is a group of formula (a)

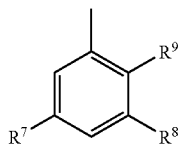
(a)

wherein
R$^7$ is hydrogen, (C$_1$-C$_5$)-alkyl or O—(C$_1$-C$_4$)-alkyl;
R$^8$ is OH, pyrrolidonyl or —C(O)NR$^5$R$^6$ wherein R$^5$ is hydrogen or (C$_1$-C$_5$)-alkyl and R$^6$ is (C$_1$-C$_5$)-alkyl or (C$_1$-C$_5$)-alkyl substituted by phenyl, and
R$^9$ is hydrogen or (C$_1$-C$_5$)-alkyl.

In another embodiment the present invention provides a compound of formula I wherein R$^1$ is a group of formula (a) wherein R$^7$ is hydrogen or (C$_1$-C$_5$)-alkyl; R$^8$ is —C(O)NR$^5$R$^6$ wherein R$^5$ is hydrogen or (C$_1$-C$_5$)-alkyl and R$^6$ is (C$_1$-C$_5$)-alkyl or —CH$_2$-phenyl; and R$^9$ is hydrogen.

In still another embodiment the present invention provides a compound of formula I wherein R$^1$ is a group of formula (a) wherein R$^7$ is hydrogen or (C$_1$-C$_5$)-alkyl; R$^8$ is —C(O)NR$^5$R$^6$ wherein R$^6$ are (C$_1$-C$_5$)-alkyl; and R$^9$ is hydrogen.

In another embodiment the present invention provides a compound of formula I wherein R$^1$ is a group of formula (a) wherein R$^7$ is hydrogen or O—(C$_1$-C$_4$)-alkyl; R$^8$ is OH or pyrrolidonyl; and R$^9$ is hydrogen or (C$_1$-C$_5$)-alkyl.

In one embodiment the present invention provides a compound of formula I wherein R$^1$ is heteroaryl. In another embodiment the present invention provides a compound of formula I wherein R$^1$ is indolyl substituted by (C$_1$-C$_5$)-alkyl or is quinolinyl. In still another embodiment the present invention provides a compound of formula I wherein R$^1$ is 1-butyl-indol-6-yl or quinolin-2-yl.

In one embodiment the present invention provides a compound of formula I wherein R$^2$ is phenyl which is unsubstituted or substituted with fluorine. In another embodiment the present invention provides a compound of formula I wherein R$^2$ is (C$_1$-C$_5$)-alkyl which is unsubstituted or unsubstituted or substituted with S—(C$_1$-C$_5$)-alkyl.

In one embodiment the present invention provides a compound of formula I wherein R$^3$ is hydrogen, (C$_1$-C$_5$)-alkyl or phenyl. In another embodiment the present invention provides a compound of formula I wherein R$^3$ is hydrogen; (C$_1$-C$_5$)-alkyl which is unsubstituted or substituted by phenyl, COOH or COOCH$_3$; or phenyl. In still another embodiment the present invention provides a compound of formula I wherein R$^3$ is hydrogen, methyl, ethyl, isopropyl, phenyl, benzyl, CH$_2$COOH or CH$_2$COOCH$_3$. In still another embodiment the present invention provides a compound of formula I wherein R$^3$ is methyl.

In one embodiment the present invention provides a compound of formula I wherein R$^4$ is unsubstituted (C$_1$-C$_6$)-alkyl or is (C$_1$-C$_6$)-alkyl substituted by one or more substituents selected from halogen, N[(C$_1$-C$_6$)-alkyl]$_2$, (C$_3$-C$_6$)-cycloalkyl, unsubstituted phenyl, phenyl substituted by one or more (C$_1$-C$_5$)-alkyl, and isoxazolyl substituted by one or more (C$_1$-C$_5$)-alkyl. In another embodiment the present invention provides a compound of formula I wherein R$^4$ is unsubstituted (C$_1$-C$_6$)-alkyl. In still another embodiment the present invention provides a compound of formula I wherein R$^4$ is isopropyl, isobutyl, isopentyl or isohexyl. In another embodiment the present invention provides a compound of formula I wherein R$^4$ is (C$_1$-C$_6$)-alkyl substituted by one or more substituents selected from halogen, N[(C$_1$-C$_6$)-alkyl]$_2$, (C$_3$-C$_6$)-cycloalkyl, unsubstituted phenyl, phenyl substituted by one or more (C$_1$-C$_5$)-alkyl, and isoxazolyl substituted by one or more (C$_1$-C$_5$)-alkyl. In another embodiment the present invention provides a compound of formula I wherein R$^4$ is methyl substituted by phenyl or by isoxazolyl substituted by methyl; ethyl substituted by cyclohexyl, phenyl or dimethylamino; propyl substituted by phenyl or dimethylphenyl; or butyl substituted by fluorine.

In one embodiment the present invention provides a compound of formula I wherein R$^4$ is cyclohexyl.

In one embodiment the present invention provides a compound of formula I wherein R$^4$ is unsubstituted phenyl or phenyl substituted by OH; N[(C$_1$-C$_6$)-alkyl]$_2$; unsubstituted (C$_1$-C$_6$)-alkyl (C$_1$-C$_6$)-alkyl substituted by halogen, O—(C$_1$-C$_4$)-alkyl or COO(C$_1$-C$_5$)-alkyl.

In one embodiment the present invention provides a compound of formula I wherein R$^4$ is phenyl. In another embodiment the present invention provides a compound of formula I wherein R$^4$ is phenyl substituted by OH, dimethylamino, methyl, isobutyl, tri-fluoromethyl, methoxy, ethoxy or COO-methyl.

In one embodiment the present invention provides a compound of formula I wherein R$^4$ is unsubstituted pyridyl or pyridyl substituted by methyl.

In one embodiment the present invention provides a compound of formula I wherein
R$^1$ is a group of formula (a) wherein
R$^7$ is hydrogen, (C$_1$-C$_5$)-alkyl or O—(C$_1$-C$_4$)-alkyl;
R$^8$ is OH, pyrrolidonyl or —C(O)NR$^5$R$^6$ wherein R$^5$ is hydrogen or (C$_1$-C$_5$)-alkyl and R$^6$ is (C$_1$-C$_5$)-alkyl or (C$_1$-C$_5$)-alkyl substituted by phenyl, and
R$^9$ is hydrogen or (C$_1$-C$_5$)-alkyl;
R$^2$ is phenyl which is unsubstituted or substituted with fluorine or is (C$_1$-C$_5$)-alkyl which is unsubstituted or substituted with S—(C$_1$-C$_5$)-alkyl;
R$^3$ is hydrogen, (C$_1$-C$_5$)-alkyl or phenyl; and
R$^4$ is unsubstituted (C$_1$-C$_6$)-alkyl; (C$_1$-C$_6$)-alkyl substituted by one or more substituents selected from halogen, N[(C$_1$-C$_6$)-alkyl]$_2$, (C$_3$-C$_6$)-cycloalkyl, unsubstituted phenyl, phenyl substituted by one or more (C$_1$-C$_5$)-alkyl, and isoxazolyl substituted by one or more (C$_1$-C$_5$)-alkyl; cyclohexyl; unsubstituted phenyl or phenyl substituted by OH, N[(C$_1$-C$_6$)-alkyl]$_2$, unsubstituted (C$_1$-C$_6$)-alkyl, (C$_1$-C$_6$)-alkyl substituted by halogen, O—(C$_1$-C$_4$)-alkyl or COO(C$_1$-C$_5$)-alkyl; or is unsubstituted pyridyl or pyridyl substituted by methyl.

In another embodiment the present invention provides a compound of formula I wherein
$R^1$ is a group of formula (a) wherein
$R^7$ and $R^9$ are hydrogen; and
$R^8$ is —C(O)NR$^5$R$^6$ wherein $R^5$ is hydrogen or $(C_1-C_5)$-alkyl and $R^6$ is $(C_1-C_5)$-alkyl or $(C_1-C_5)$-alkyl substituted by phenyl;
$R^2$ is phenyl;
$R^3$ is hydrogen, $(C_1-C_5)$-alkyl or phenyl; and
$R^4$ is unsubstituted $(C_1-C_6)$-alkyl; $(C_1-C_6)$-alkyl substituted by one or more substituents selected from halogen, $N[(C_1-C_6)$-alkyl$]_2$, $(C_3-C_6)$-cycloalkyl, unsubstituted phenyl, phenyl substituted by one or more $(C_1-C_5)$-alkyl, and isoxazolyl substituted by one or more $(C_1-C_5)$-alkyl; cyclohexyl; unsubstituted phenyl or phenyl substituted by OH, $N[(C_1-C_6)$-alkyl$]_2$, unsubstituted $(C_1-C_6)$-alkyl, $(C_1-C_6)$-alkyl substituted by halogen, O—$(C_1-C_4)$-alkyl or $COO(C_1-C_5)$-alkyl; or is unsubstituted pyridyl or pyridyl substituted by methyl.

In one embodiment the present invention provides a compound of formula I wherein
$R^1$ is indolyl substituted by $(C_1-C_5)$-alkyl, or quinolinyl;
$R^2$ is phenyl;
$R^3$ is $(C_1-C_5)$-alkyl; and
$R^4$ is phenyl.

In one embodiment the present invention provides compound of formula I selected from
{(R)-1-[3-(methyl-propyl-carbamoyl)-benzoylamino]-2-phenyl-ethyl}-(2-phenylcarbamoyl-propyl)-phosphinic acid,
{(R)-1-[3-(methyl-pentyl-carbamoyl)-benzoylamino]-2-phenyl-ethyl}-(2-phenylcarbamoyl-propyl)-phosphinic acid,
[(R)-1-(3-dipentylcarbamoyl-benzoylamino)-2-phenyl-ethyl]-(2-phenylcarbamoyl-propyl)-phosphinic acid,
[(R)-1-(3-dipropylcarbamoyl-5-methyl-benzoylamino)-2-phenyl-ethyl]-(2-phenylcarbamoyl-propyl)-phosphinic acid,
{(R)-1-[3-(2-oxo-pyrrolidin-1-yl)-5-propoxy-benzoylamino]-2-phenyl-ethyl}-(2-phenylcarbamoyl-propyl)-phosphinic acid,
{(R)-1-[(1-butyl-1H-indole-6-carbonyl)-amino]-2-phenyl-ethyl}-(2-phenylcarbamoyl-propyl)-phosphinic acid,
[1-(3-dipropylcarbamoyl-benzoylamino)-2-phenyl-ethyl]-(2-p-tolylcarbamoyl-butyl)-phosphinic acid,
[1-(3-dipropylcarbamoyl-benzoylamino)-2-phenyl-ethyl]-(3-methyl-2-p-tolylcarbamoyl-butyl)-phosphinic acid,
[1-(3-dipropylcarbamoyl-benzoylamino)-2-phenyl-ethyl]-(2-phenyl-2-p-tolylcarbamoyl-ethyl)-phosphinic acid,
[(R)-1-(3-dipropylcarbamoyl-benzoylamino)-2-phenyl-ethyl]-(2-phenylcarbamoyl-propyl)-phosphinic acid,
[(R)-1-(3-dipropylcarbamoyl-benzoylamino)-2-phenyl-ethyl]-((S)-2-phenylcarbamoyl-propyl)-phosphinic acid,
[(R)-1-(3-dipropylcarbamoyl-benzoylamino)-2-phenyl-ethyl]-(2-p-tolylcarbamoyl-propyl)-phosphinic acid,
[(R)-1-(3-dipropylcarbamoyl-benzoylamino)-2-phenyl-ethyl]-((S)-2-p-tolylcarbamoyl-propyl)-phosphinic acid,
[(R)-1-(3-dipropylcarbamoyl-benzoylamino)-2-phenyl-ethyl]-((R)-2-p-tolylcarbamoyl-propyl)-phosphinic acid,
[(R)-1-(3-dipropylcarbamoyl-benzoylamino)-2-phenyl-ethyl]-(2-isobutylcarbamoyl-propyl)-phosphinic acid,
[(R)-1-(3-dipropylcarbamoyl-benzoylamino)-2-phenyl-ethyl]-[2-(3-methyl-butylcarbamoyl)-propyl]-phosphinic acid,
[2-(3,3-dimethyl-butylcarbamoyl)-propyl]-[(R)-1-(3-dipropylcarbamoyl-benzoylamino)-2-phenyl-ethyl]-phosphinic acid,
[(R)-1-(3-dipropylcarbamoyl-benzoylamino)-2-phenyl-ethyl]-[2-(4,4,4-trifluoro-butyl-carbamoyl)-propyl]-phosphinic acid,
[(R)-1-(3-dipropylcarbamoyl-benzoylamino)-2-phenyl-ethyl]-[2-(3,3,4,4-tetrafluoro-butylcarbamoyl) -propyl]-phosphinic acid,
[(R)-1-(3-dipropylcarbamoyl-benzoylamino)-2-phenyl-ethyl]-[2-(2,2,3,3,4,4,4-heptafluoro-butylcarbamoyl) -propyl]-phosphinic acid,
(2-cyclohexylcarbamoyl-propyl)-[(R)-1-(3-dipropylcarbamoyl-benzoylamino)-2-phenyl-ethyl]-phosphinic acid,
[2-(2-cyclohexyl-ethylcarbamoyl)-propyl]-[(R)-11-(3-dipropylcarbamoyl-benzoylamino)-2-phenyl-ethyl]-phosphinic acid,
[(R)-1-(3-dipropylcarbamoyl-benzoylamino)-2-phenyl-ethyl]-[2-(4-hydroxy-phenylcarbamoyl)-propyl]-phosphinic acid,
[(R)-1-(3-dipropylcarbamoyl-benzoylamino)-2-phenyl-ethyl]-[2-(4-methoxy-phenyl-carbamoyl)-propyl]-phosphinic acid,
[(R)-1-(3-dipropylcarbamoyl-benzoylamino)-2-phenyl-ethyl]-[2-(pyridin-2-ylcarbamoyl)-propyl]-phosphinic acid,
[(R)-1-(3-dipropylcarbamoyl-benzoylamino)-2-phenyl-ethyl]-[2-(5-methyl-pyridin-2-ylcarbamoyl)-propyl]-phosphinic acid and
(2-benzylcarbamoyl-propyl)-[(R)-1-(3-dipropylcarbamoyl-benzoylamino)-2-phenyl-ethyl]-phosphinic acid.

In another embodiment the present invention provides a process for the preparation of compounds of formula I comprising reacting a compound of formula II

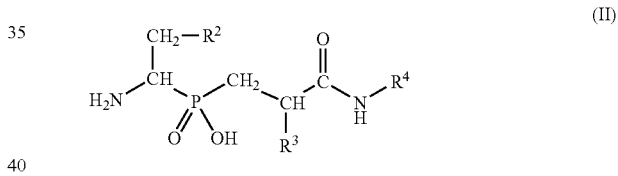

wherein
$R^2$ is $(C_1-C_5)$-alkyl or phenyl;
$R^3$ is hydrogen, $(C_1-C_5)$-alkyl, O—$(C_1-C_5)$-alkyl or phenyl; and
$R^4$ is $(C_1-C_6)$-alkyl, $(C_3-C_6)$-cycloalkyl, phenyl, pyridyl, or indolyl;

with a compound of formula III

$$R^1\text{—}COR^{10} \qquad (III)$$

wherein
$R^1$ is aryl or heteroaryl; and
$R^{10}$ is halogen or OH;

and, if desired, converting the resulting compound into a pharmaceutically acceptable salt.

The reaction may take place in the presence of an activating agent and an additive.

Examples for an activating agent include dicyclohexylcarbodiimide and N-(3-dimethylaminopropyl)-N'-ethyl-carbodiimide hydrochloride. Examples for an additive include 1-hydroxy-benzotriazole. A base, e.g. a trialkylamine, e.g. triethylamine, may be present. The reaction may take place in the presence of a solvent, e.g. an ether, e.g. tetrahydrofurane. The temperature may be in the range of from 20° C. to 60° C., or of from 20° C. to 40° C.

The compounds of formula III are commercially available or may be prepared according to procedures known to the skilled artisan, e.g. N-methyl-N-propyl-isophthalamic acid, N,N-dipropyl-isophthalamic acid, 5-methyl-N,N-dipropyl-isophthalamic acid, N-pentyl-N-propyl-isophthalamic acid and N,N-dipentyl-isophthalamic acid may be prepared according to a procedure as disclosed in Taylor and Spooner, J. of Agricultural and Food Chemistry, 38:1422-1427 (1990); 3-(2-oxo-pyrrolidin-1-yl)-5-propoxy-benzoic acid may be prepared according to the procedure as disclosed in WO 03/045,913; and 1-butyl-indole-6-carboxylic acid may be prepared as disclosed in WO 03/040,096.

The compounds of formula II are new and also an embodiment of the present invention.

Compounds of formula II can be prepared by reacting a compound of formula IV

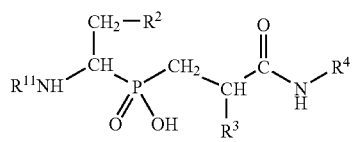

(IV)

wherein $R^{11}$ is a protecting group, e.g. Boc, and $R^2$, $R^3$ and $R^4$ have the above meanings, with a strong mineral acid, e.g. aqueous HI, HCl or HBr, or with, e.g., trifluoroacetic acid, in a solvent, e.g. $CH_2Cl_2$, at a temperature in the range of from 20° C. to 100° C., or at 20° C.

The compounds of formula IV are new and also an embodiment of the present invention.

Compounds of formula IV can be prepared by reacting a compound of formula V

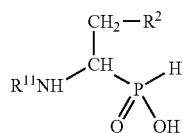

(V)

wherein $R^{11}$ and $R^2$ have the above meanings, with a compound of formula VI

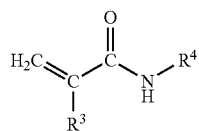

(VI)

wherein $R^3$ and $R^4$ have the above meanings.

Michael addition of the phosphinic acids, i.e. compounds of formula V, to the acryl-amides, compounds of formula VI [Liu et al., J. Organomet. Chem. 646:212 (2002)] can be effected in the presence of hexamethyldisilazane at a temperature in the range of from 20° C. to 150° C., or at, e.g., 110° C.

The compounds of formula VI are known or can be prepared by methods known in the art, e.g. by treatment of the malonic acids, compounds of formula VII

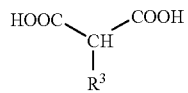

(VII)

with formaldehyde and $HN(Et)_2$ (Liu et al. above) followed by conversion of the acrylic acids to the acrylamides. The compounds of formula VII are commercially available.

Compounds of formula V may be prepared by reacting a compound of formula VIII

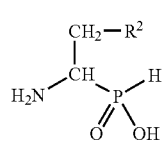

(VIII)

with a compound of formula $R^{11}$—O—$R^{11}$, wherein $R^{11}$ is a protecting group, e.g. Boc, e.g. with $(Boc)_2O$ [Sampson and Bartlett, Biochemistry 30:2255 (1991)] and a base such as an alkylamine, e.g., $NEt_3$, in a solvent like $CH_2Cl_2$ or MeOH, at a temperature in the range of from 0° C. to 50° C., or, e.g., at 22° C. The compounds of formula V can be resolved using a chiral amine [Sampson and Bartlett, Biochemistry 30:2255 (1991)] such as α-(+)-methyl-benzylamine, in a solvent mixture like a ketone and an alcohol, e.g., methylethylketone and MeOH, to give the corresponding salts which can be recrystallized from the same solvent mixture as described above. Desalting affords the enantiomerically pure (>95%) (R)-enantiomers of the compounds of formula V. Novel compounds of formula V, e.g. compounds V-2 and V-5 below, are also an embodiment of the present invention.

The compounds of formula VIII can be prepared by reacting a compound of formula IX

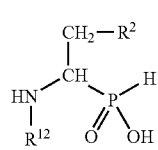

(IX)

wherein $R^{12}$ is diphenylmethyl with a strong mineral acid such as HI, HCl or HBr, e.g. aqueous HBr, at a temperature in the range of from 50° C. to 100° C., e.g., at 100° C. or at 105° C. Novel compounds of formula VIII, e.g. compounds VIII-2 and VIII-4 below, are also an embodiment of the present invention.

The compounds of formula IX can be prepared by reacting a compound of formula X

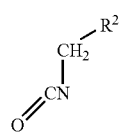

(X)

with a protected amine, e.g. diphenylmethylamine hydrochloride, and phosphinic acid, e.g., 50% aqueous phosphinic acid [Baylis et al., J. Chem. Soc., Perkin Trans. 1:2845 (1984)] in a solvent like water or dioxane, at a temperature in the range of from 50° C. to 100° C., e.g., at 100° C. The compounds of formula X are commercially available, except for $R^2$ is 3,5-difluorophenyl, the preparation of which is described herein. Novel compounds of formula IX, e.g. compounds IX-2 and IX-4 below, are also an embodiment of the present invention.

In another embodiment the present invention provides a process for the preparation of compounds of formula I comprising reacting a compound of formula XI

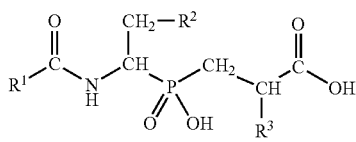

(XI)

wherein
R$^1$ is aryl or heteroaryl;
R$^2$ is (C$_1$-C$_5$)-alkyl or phenyl;
R$^3$ is hydrogen, (C$_1$-C$_5$)-alkyl, O—(C$_1$-C$_5$)-alkoxy or phenyl;
with a compound of formula XII $H_2N—R^4$ (XII)

wherein
R$^4$ is (C$_1$-C$_6$)-alkyl, (C$_3$-C$_6$)-cycloalkyl, phenyl, pyridyl or indolyl, and, if desired, converting the resulting compound into a pharmaceutically acceptable salt.

The reaction may take place in the presence of an activating agent and an additive.

Examples for an activating agent include dicyclohexylcarbodiimide and N-(3-dimethylaminopropyl)-N'-ethyl-carbodiimide hydrochloride. Examples for an additive include 1-hydroxy-benzotriazole. A base, e.g. a trialkylamine, e.g. triethylamine, may be present. The reaction may take place in the presence of a solvent, e.g. an ether, e.g. tetrahydrofurane. The temperature may be in the range of from 20° C. to 60° C., or of from 20° C. to 40° C.

The compounds of formula XII are commercially available or may be prepared according to procedures known to the skilled artisan, e.g. H$_2$N(CH$_2$)$_3$CF$_3$ may be prepared according to Dijols et al., Biochemistry 41:9286-9292 (2002); H$_2$N(CH$_2$)$_2$CF$_2$CHF$_2$ may be prepared from the corresponding bromide via the phthalimide method according to Jacobs et al., J. Med. Chem. 37:1282 (1994); phenethylamine derivatives may be prepared according to Bailey et al., Can. J. of Chem. 49:3143-51 (1971) and isoxazole derivatives may be prepared according to WO 03/072,535.

The compounds of formula XI are new and also an embodiment of the present invention.

Compounds of formula XI can be prepared by hydrolysing a compound of formula XIII

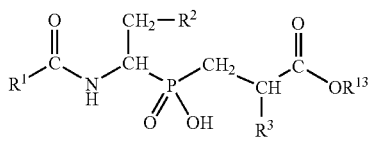

(XIII)

wherein R$^{13}$ is (C$_1$-C$_4$)-alkyl,
in the presence of a base such as a KOH, NaOH or LiOH, in a solvent like methanol or water, or a mixture of both, at a temperature in the range of from 0° C. to 60° C., e.g., at 20° C.

The compounds of formula XIII are new and also an embodiment of the present invention.

Compounds of formula XIV can be prepared by reacting a compound of formula XIV

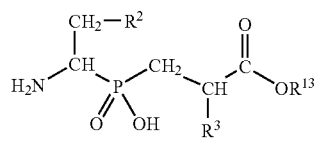

(XIV)

with a compound of formula III in the presence of an activating agent such as dicyclohexylcarbodiimide or N-(3-dimethylaminopropyl)-N'-ethyl-carbodiimide hydrochloride, and an additive such as 1-hydroxy-benzotriazole and a base such as a trialkyl amine, e.g., N(Et)$_3$, in a solvent, such as an ether, e.g., tetrahydrofurane, at a temperature in the range of from 20° C. to 60° C., e.g. of from 20° C. to 40° C.

The compounds of formula XIV are new and also an embodiment of the present invention. Compounds of formula XIV can be prepared by reacting a compound of formula XV

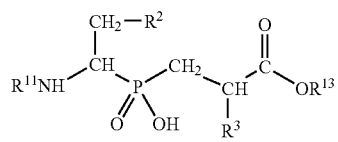

(XV)

wherein R$^{11}$ is a protecting group, e.g. Boc, with a strong mineral acid such as aqueous HI, HCl or HBr, or with, e.g., trifluoroacetic acid, in a solvent like CH$_2$Cl$_2$, at a temperature in the range of from 20° C. to 100° C., e.g. at 20° C.

The compounds of formula XV are new and also an embodiment of the present invention. Compounds of formula XV can be prepared by reacting a compound of formula V with a compound of formula XVI

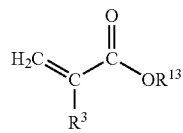

(XVI)

in the presence of, e.g., hexamethyldisilazane, at a temperature in the range of from 20° C. to 150° C., e.g., at 110° C. (Michael addition, Liu et al. above). The compounds of formula XVI are commercially available.

EXAMPLES

General: Stereo descriptors R and S (according to the CIP-rule) are given in the systematic names. If no descriptors are given mixtures of isomers are obtained. The following abbreviations were used: Boc: t-butyloxycarbonyl; TFA: trifluoroacetic acid.

Example S1

Preparation of Starting Compounds of Formula V (a) Preparation of Compounds of Formula IX To a suspension of 36.3 g of diphenylmethylamine hydrochloride in 80 ml of water 180 ml of a 50% aqueous solution of $H_3PO_2$ were added. The mixture was heated to reflux temperature and treated with a solution of 200 mmol of the appropriate compound of formula X in 30 ml of dioxane over 10 min and stirring was continued for 10 min. The suspension was cooled to 65° C., filtered and the solid was washed once with water. The wet solid was stirred with 180 ml of acetone at 0° C. for 10 min, the suspension was filtered, the solid was washed once with cold acetone and dried to give the desired compound of formula IX in 50 to 70% yield.

| No. | Compound of formula IX | MS |
|---|---|---|
| IX-1 | [1-(benzhydryl-amino)-3-methyl-butyl]-phosphinic acid | 316.3 (M − H)⁻ |
| IX-2 | [1-(benzhydryl-amino)-3-methylsulfanyl-butyl]-phosphinic acid | 348.3 (M − H)⁻ |
| IX-3 | [1-(benzhydryl-amino)-2-phenyl-ethyl]-phosphinic acid | 350.3 (M − H)⁻ |
| IX-4[1] | [1-(benzhydryl-amino)-2-(3,5-difluoro-phenyl)-ethyl]-phosphinic acid | 386.2 (M − H)⁻ |

[1] The starting aldehyde was prepared as follows: A solution of 5.3 g of 3,5-difluorophenyl-acetic acid in 40 ml of MeOH and 3 ml of $BF_3 \cdot Et_2O$ was warmed to 50° C. for 1 h. The solution was evaporated, the residue partitioned between $Et_2O$ and aqueous $NaHCO_3$, the organic layer was washed with water, dried and evaporated. The remaining methylester (5.6 g) was dissolved in 240 ml of dry toluene, cooled to −78° C. and treated with 45 ml of a 1M solution of diisobutylaluminum hydride in $CH_2Cl_2$ and stirring was continued at −78° C. for 1 h. The mixture was quenched with 30 ml of MeOH and 100 ml of a 50% aqueous solution of sodium-potassium tartrate and extracted with $Et_2O$. The organic layer was washed with brine, dried and evaporated to give 4.5 g of (3,5-difluoro-phenyl)-acetaldehyde.

(b) Preparation of Compounds of Formula VIII

A suspension of 77.4 mmol of the appropriate compound of formula 1× and 210 ml of 48% aqueous HBr was heated to 105° C. for 1 h. The mixture was washed several times with $Et_2O$ and the aqueous solution was evaporated to dryness. The resulting solid was dissolved in 465 ml of ethanol. The solution was treated with 29 ml of propylenoxide and the suspension obtained was stirred at 20° C. overnight. The suspension was filtered, the solid washed with cold ethanol and dried to give the desired compound of formula VIII in 70 to 95% yield.

| No. | Compound of formula VIII | MS |
|---|---|---|
| VIII-1 | (1-amino-3-methyl-butyl)-phosphinic acid | 150.1 (M − H)⁻ |
| VIII-2 | (1-amino-3-methylsulfanyl-butyl)-phosphinic acid | 184.1 (M + H)⁺ |
| VIII-3 | (1-amino-2-phenyl-ethyl)-phosphinic acid | 185.9 (M + H)⁺ |
| VIII-4 | [1-amino-2-(3,5-difluoro-phenyl)-ethyl]-phosphinic acid | 220.1 (M − H)⁻ |

(c) Preparation of Compounds of Formula V

To a solution of 2.0 mmol of the appropriate compound of formula VIII in 10 ml of MeOH a solution of 2.2 mmol of $(Boc)_2O$ in 2 ml of MeOH was added at 20° C. and stirring was continued for 4 h. The mixture was evaporated and the residue partitioned between AcOEt and aqueous $KHSO_4$ (10%). The organic layer was washed with brine, dried and evaporated to give the crude desired compound of formula V in 80 to 90% yield. Resolution of the racemate was accomplished by crystallization of 2 mmol of a compound of formula V and 2.2 mmol of α-(+)-methylbenzylamine in 40 ml of methylethylketone followed by recrystallization. The salt obtained was partitioned between aqueous hydrochloric acid and AcOEt to the (R)-enantiomer of a compound of formula V in 30 to 40% yield and 95% optical purity.

| No. | Compound of formula V | MS/α[D]* |
|---|---|---|
| V-1 | (1-tert-butoxycarbonylamino-3-methyl-butyl)-phosphinic acid | 250.1 (M − H)⁻ |
| V-2 | (1-tert-butoxycarbonylamino-3-methylsulfanyl-butyl)-phosphinic acid | 282.1 (M − H)⁻ |
| V-3 | (1-tert-butoxycarbonylamino-2-phenyl-ethyl)-phosphinic acid | 284.4 (M − H)⁻ |
| V-4 | ((R)-1-tert-butoxycarbonylamino-2-phenyl-ethyl)-phosphinic acid | 284.1 (M − H)⁻ α[D] −29.4° |
| V-5 | [1-tert-butoxycarbonylamino-2-(3,5-difluoro-phenyl)-ethyl]-phosphinic acid | 320.4 (M − H)⁻ |

*α[D] (1%, EtOH)

Example S2

Preparation of Compounds of Formula VI

A mixture of 28 mmol of the appropriate compound of formula VII and 2.9 ml of diethylamine was treated with 11 ml of formalin and heated to reflux temperature for 1-3 h. The solution was cooled to 20° C. diluted with $CH_2Cl_2$ and washed with aqueous $NaHCO_3$. The aqueous layer was acidified to pH=1 using diluted hydrochloric acid and extracted with $CH_2Cl_2$. The combined organic layers were dried and evaporated to give the corresponding crude acrylic acid in 70 to 80% yield. To a solution of 4.3 mmol of the acrylic acid in 7 ml of tetrahydrofurane 560 mg of p-toluidine, 1.8 ml of $NEt_3$, 950 mg of 1-hydroxybenzotriazole and 1.28 g of N-(3-dimethylaminopropyl)-N'-ethyl-carbodiimide hydrochloride were subsequently added and the suspension was stirred at 20° C. for 1-3 h. The mixture was partitioned between aqueous sat. $NH_4Cl$ and AcOEt, the organic layer was washed with 0.5 N aqueous NaOH, dried and evaporated. The crude material was chromatographed on silica using n-heptane/AcOEt to give the desired compound of formula VI in 50 to 70% yield.

| No. | Compound of formula VI | MS |
|---|---|---|
| VI-1 | N-phenylmethacrylamide | |
| VI-2 | 2-methylene-N-p-tolyl-butyramide | 190.3 (M + H)⁺ |
| VI-3 | 3-methyl-2-methylene-N-p-tolyl-butyramide | 204.1 (M + H)⁺ |
| VI-4 | 2-benzyl-N-p-tolyl-acrylamide | 252.1 (M + H)⁺ |
| VI-5 | 3-phenylcarbamoyl-but-3-enoic acid methyl ester | 219.7 (M)⁺ |
| VI-6 | N-(3-ethoxy-phenyl)-acrylamide | |
| VI-7 | N-(3-trifluoromethyl-phenyl)-acrylamide | |
| VI-8 | N-(5-methyl-pyridin-2-yl)-acrylamide | |
| VI-9 | N-(4-tert-butyl-phenyl)-acrylamide | |
| VI-10 | N-(4-dimethylamino-phenyl)-acrylamide | |
| VI-11 | N-(4-hydroxy-phenyl)-acrylamide | |
| VI-12 | 4-acryloylamino-benzoic acid methyl ester | |
| VI-13 | N-(3,4-dimethoxy-phenyl)-acrylamide | |
| VI-14 | N-(3,5-dimethoxy-phenyl)-acrylamide | |
| VI-15 | N-(3,4,5-trimethoxy-phenyl)-acrylamide | |
| VI-16 | N-(α-phenylethyl)-acrylamide | |
| VI-17 | N-(2-dimethylamino-ethyl)-acrylamide | |

Example S3

Preparation of N,N-dipropyl-isophthalamic Acid Chloride

A solution of 1.30 g of N,N-dipropyl-isophthalamic acid and 1.9 ml of $SOCl_2$ in 5 ml of benzene was heated to reflux temperature until gas evolution ceased (30 min). The solution was evaporated and the residue co-distilled with toluene to give 1.41 g of the N,N-dipropyl-isophthalamic acid chloride.

Example S4

Preparation of a Compound of Formula XI, i.e. 3-{[(R)-1-(3-dipropylcarbamoyl-benzoylamino)-2-phenyl-ethyl]-hydroxy-phosphinoyl}-2-methyl-propionic Acid (a) Preparation of 3-[((R)-1-tert-butoxycarbonylamino-2-phenyl-ethyl)-hydroxy-phosphinoyl]-2-methyl-propionic Acid Methyl Ester A mixture of 5.00 g of ((R)-1-tert-butoxycarbonylamino-2-phenyl-ethyl)-phosphinic acid and 18.3 ml of $HN(TMS)_2$ was heated to 110° C. for 1 h. To the solution was added 2.5 ml of methyl methacrylate and heating was continued at 110° C. for 2 h. The solution was cooled to 70° slowly diluted with 10 ml of EtOH and evaporated. The residue was chromatographed on silica using a gradient of $CH_2Cl_2$/MeOH (9:1)→$CH_2Cl_2$/MeOH/AcOH (10:1:0.3) to give 4.10 g of the title compound. MS: 386.5 $(M+H)^+$.

(b) Preparation of 3-[((R)-1-amino-2-phenyl-ethyl)-hydroxy-phosphinoyl]-2-methyl-propionic Acid Methyl Ester; Salt with Trifluoro-acetic Acid A solution of 1.75 g of 3-[((R)-1-tert-butoxycarbonylamino-2-phenyl-ethyl)-hydroxy-phosphinoyl]-2-methyl-propionic acid methyl ester and 3.40 ml of $CF_3COOH$ in 20 ml of $CH_2Cl_2$ was stirred at 20° C. for 16 h and evaporated to give 2.23 g of the crude title compound.

(c) Preparation of 3-{[(R)-1-(3-dipropylcarbamoyl-benzoylamino)-2-phenyl-ethyl]-hydroxy-phosphinoyl}-2-methyl-propionic Acid Methyl Ester To a solution of 2.23 g of the crude amine as TFA salt (a compound of formula XIV) in 15 ml of dioxane, 1.9 ml of $NEt_3$ and a solution of 1.47 g of N,N-dipropyl-isophthalamic acid chloride in 2 ml of dioxane were subsequently added at 0° C. and stirring was continued at 20° C. for 3 h. The mixture was partitioned between AcOEt and brine and the pH adjusted to 2 using hydrochloric acid. The organic layer was washed with brine, dried and evaporated. The residue was chromatographed on silica using a gradient of $CH_2Cl_2$→$CH_2Cl_2$/MeOH/AcOH (10:1:0.5) to give 2.15 g of the title compound. MS: 515.3 $(M-H)^-$.

(d) Preparation of 3-{[(R)-1-(3-dipropylcarbamoyl-benzoylamino)-2-phenyl-ethyl]-hydroxy-phosphinoyl}-2-methyl-propionic Acid A solution of 2.11 g of 3-{[(R)-1-(3-dipropylcarbamoyl-benzoylamino)-2-phenyl-ethyl]-hydroxy-phosphinoyl}-2-methyl-propionic acid methyl ester in 8 ml of MeOH was treated with a solution of 865 mg of $LiOH.H_2O$ in 2 ml of $H_2O$ and the turbid solution was stirred at 20° C. for 1.5 h. The mixture was evaporated and the residue partitioned between aqueous HCl (pH=2) and AcOEt. The organic layer was washed with brine, dried and evaporated to give 1.54 g of the title compound. MS: 501.4 (M–H)—.

Example 1

Preparation of Compounds of Formula I Starting from a Compound of Formula II and a Compound of Formula III (a) A mixture of 0.4 mmol of the appropriate compound of formula V and 0.6 ml of $HN(TMS)_2$ was heated to 110° C. for 1 h. To the solution 0.6 mmol of the appropriate compound of formula VI was added and heating was continued at 110° C. for 1-4 h. The solution was cooled to 20°, diluted with 1 ml of EtOH and evaporated. The residue was chromatographed on silica using a gradient of $CH_2Cl_2$/MeOH (9:1)→$CH_2Cl_2$/MeOH/-AcOH (10:1:0.5) to give the desired compound of formula IV in 30 to 70% yield.

| No. | Compound of formula IV | MS |
|---|---|---|
| IV-1 | (1-tert-butoxycarbonylamino-3-methyl-butyl)-(2-phenylcarbamoyl-propyl)-phosphinic acid | 411.5 $(M - H)^-$ |
| IV-2 | (1-tert-butoxycarbonylamino-3-methylsulfanyl-butyl)-(2-phenylcarbamoyl-propyl)-phosphinic acid | 443.4 $(M - H)^-$ |
| IV-3 | (1-tert-butoxycarbonylamino-2-phenyl-ethyl)-(2-p-tolylcarbamoyl-propyl)-phosphinic acid | 459.1 $(M - H)^-$ |
| IV-4 | ((R)-1-tert-butoxycarbonylamino-2-phenyl-ethyl)-(2-p-tolylcarbamoyl-propyl)-phosphinic acid | 459.1 $(M - H)^-$ |
| IV-5 | (1-tert-butoxycarbonylamino-2-phenyl-ethyl)-(2-p-tolylcarbamoyl-butyl)-phosphinic acid | 475.3 $(M + H)^+$ |
| IV-6 | (1-tert-butoxycarbonylamino-2-phenyl-ethyl)-(3-methyl-2-p-tolylcarbamoyl-butyl)-phosphinic acid | 489.1 $(M + H)^+$ |
| IV-7[1] | (1-tert-butoxycarbonylamino-2-phenyl-ethyl)-(2-phenyl-2-p-tolylcarbamoyl-ethyl)-phosphinic acid | 522.3 $(M)^+$ |
| IV-8 | (1-tert-butoxycarbonylamino-2-phenyl-ethyl)-(3-phenyl-2-p-tolylcarbamoyl-propyl)-phosphinic acid | 537.4 $(M + H)^+$ |
| IV-9 | 3-[(1-tert-butoxycarbonylamino-2-phenyl-ethyl)-hydroxy-phosphinoylmethyl]-N-phenyl-succinamic acid methyl ester | 505.3 $(M + H)^+$ |
| IV-10 | [1-tert-butoxycarbonylamino-2-(3,5-difluoro-phenyl)-ethyl]-(2-phenylcarbamoyl-propyl)-phosphinic acid | 481.8 $(M - H)^-$ |

[1]Compound IV-7 was prepared by an inverse sequence of reactions, i.e., the corresponding compound of formula V was reacted with 2-phenylacrylic acid to give 3-[(1-tert-butoxycarbonylamino-2-phenyl-ethyl)-hydroxy-phosphinoyl]-2-phenyl-propionic acid (MS: 432.4 $(M - H)^-$), which was reacted with p-toluidine to give (1-tert-butoxycarbonylamino-2-phenyl-ethyl)-(2-phenyl-2-p-tolylcarbamoyl-ethyl)-phosphinic acid.

(b) A solution of 0.20 mmol of the appropriate compound of formula IV and 0.23 ml of $CF_3COOH$ in 2.0 ml of $CH_2Cl_2$ was stirred at 20° C. for 1.5 h and evaporated. The resulting crude compound of formula II (as TFA salt) was dissolved in 1 ml of tetrahydrofurane and subsequently treated with 0.22 mmol of the appropriate compound of formula III, 0.70 mmol of $NEt_3$, 0.24 mmol of 1-hydroxybenzotriazole and 0.26 mmol of N-(3-dimethyl-aminopropyl)-N'-ethyl-carbodiimide hydrochloride and the suspension was stirred at 20° C. for 1.5 h. The mixture was partitioned between aqueous sat. $NH_4Cl$ and AcOEt, the organic layer was washed with brine, dried and evaporated. The crude material was purified by HPLC (RP-18 column) using a gradient of $CH_3CN:H_2O$ (20:80)→$CH_3CN:H_2O$ (95:5) to give the desired compound of formula I in 30 to 40% yield.

The following compounds were prepared according to the above Example:

| No. | Compound of formula I | MS |
|---|---|---|
| I-1 | {(R)-1-[3-(methyl-propyl-carbamoyl)-benzoylamino]-2-phenyl-ethyl}-(2-phenylcarbamoyl-propyl)-phosphinic acid | 550.3 $(M + H)^+$ |
| I-2 | {(R)-1-[3-(methyl-pentyl-carbamoyl)-benzoylamino]-2-phenyl-ethyl}-(2-phenylcarbamoyl-propyl)-phosphinic acid | 578.3 $(M + H)^+$ |
| I-3 | [(R)-1-(3-dipentylcarbamoyl-benzoylamino)-2-phenyl-ethyl]-(2-phenylcarbamoyl-propyl)-phosphinic acid | 634.3 $(M + H)^+$ |
| I-4 | [(R)-1-(3-dipropylcarbamoyl-5-methyl-benzoylamino)-2-phenyl-ethyl]-(2-phenylcarbamoyl-propyl)-phosphinic acid | 592.0 $(M + H)^+$ |
| I-5 | {(R)-1-[3-(2-oxo-pyrrolidin-1-yl)-5-propoxy-benzoylamino]-2-phenyl-ethyl}-(2-phenylcarbamoyl-propyl)-phosphinic acid | 592.0 $(M + H)^+$ |
| I-6 | {(R)-1-[(1-butyl-1H-indole-6-carbonyl)-amino]-2-phenyl-ethyl}-(2-phenylcarbamoyl-propyl)-phosphinic acid | 546.2 $(M + H)^+$ |
| I-7 | (2-phenylcarbamoyl-propyl)-{(R)-2-phenyl-1-[(quinoline-2-carbonyl)-amino]-ethyl}-phosphinic acid | 502.0 $(M + H)^+$ |
| I-8 | [(R)-1-(3-hydroxy-2-methyl-benzoylamino)-2-phenyl-ethyl]-(2-phenylcarbamoyl-propyl)-phosphinic acid | 481.0 $(M + H)^+$ |
| I-9 | [1-(3-dipropylcarbamoyl-benzoylamino)-3-methyl-butyl]-(2-phenylcarbamoyl-propyl)-phosphinic acid | 542.5 $(M - H)^-$ |
| I-10 | [1-(3-dipropylcarbamoyl-benzoylamino)-3-methylsulfanyl-butyl]-(2-phenylcarbamoyl-propyl)-phosphinic acid | 574.8 $(M - H)^-$ |
| I-11 | [2-(3,5-difluoro-phenyl)-1-(3-dipropylcarbamoyl-benzoylamino)-ethyl]-(2-phenylcarbamoyl-propyl)-phosphinic acid | 612.5 $(M - H)^-$ |
| I-12 | [1-(3-dipropylcarbamoyl-benzoylamino)-2-phenyl-ethyl]-(2-p-tolylcarbamoyl-ethyl)-phosphinic acid | 578.4 $(M + H)^+$ |
| I-13 | [1-(3-dipropylcarbamoyl-benzoylamino)-2-phenyl-ethyl]-(2-p-tolylcarbamoyl-butyl)-phosphinic acid | 606.1 $(M + H)^+$ |
| I-14 | [1-(3-dipropylcarbamoyl-benzoylamino)-2-phenyl-ethyl]-(3-methyl-2-p-tolylcarbamoyl-butyl)-phosphinic acid | 620.2 $(M + H)^+$ |
| I-15 | [1-(3-dipropylcarbamoyl-benzoylamino)-2-phenyl-ethyl]-(2-phenyl-2-p-tolylcarbamoyl-ethyl)-phosphinic acid | 652.5 $(M - H)^-$ |
| I-16 | [1-(3-dipropylcarbamoyl-benzoylamino)-2-phenyl-ethyl]-(3-phenyl-2-p-tolylcarbamoyl-propyl)-phosphinic acid | 668.2 $(M + H)^+$ |
| I-17 | 3-{[1-(3-dipropylcarbamoyl-benzoylamino)-2-phenyl-ethyl]-hydroxy-phosphinoylmethyl}-N-phenyl-succinamic acid methyl ester | 636.1 $(M + H)^+$ |

Example 2

Preparation of Compounds of Formula I Starting From a Compound of Formula XI and a Compound of Formula XII The crude 3-{[(R)-1-(3-dipropylcarbamoyl-benzoylamino)-2-phenyl-ethyl]-hydroxy-phosphinoyl}-2-methyl-propionic acid (0.10 mmol) was dissolved in 0.7 ml of tetrahydrofurane and subsequently treated with 0.16 mmol of the appropriate compound of formula XII, 0.40 mmol of NEt$_3$, 0.16 mmol of 1-hydroxybenzotriazole and 0.26 mmol of N-(3-dimethylaminopropyl)-N'-ethyl-carbodiimide hydrochloride and the suspension was stirred at 45° C. for 3 h. The mixture was partitioned between aqueous sat. NH$_4$Cl and AcOEt, the organic layer was washed with brine, dried and evaporated. The crude material was purified by HPLC (RP-18 column) using a gradient of CH$_3$CN:H$_2$O (20:80)→CH$_3$CN:H$_2$O (95:5) to give the desired compound of formula I in 10-60% yield as a mixture of isomers. Separation of the isomeric mixture was accomplished by thick layer chromatography on silica using CH$_2$Cl$_2$/MeOH/AcOH 9:1:0.25. The lower running spot represents the 1(R),2(S)-stereo isomer.

The following compounds were prepared according to the above Example:

| No. | Compound of formula I | MS |
|---|---|---|
| I-18 | [(R)-1-(3-dipropylcarbamoyl-benzoylamino)-2-phenyl-ethyl]-(2-phenylcarbamoyl-propyl)-phosphinic acid | 576.6 $(M - H)^-$ |
| I-19 | [(R)-1-(3-dipropylcarbamoyl-benzoylamino)-2-phenyl-ethyl]-((S)-2-phenylcarbamoyl-propyl)-phosphinic acid | 576.6 $(M - H)^-$ |
| I-20 | [(R)-1-(3-dipropylcarbamoyl-benzoylamino)-2-phenyl-ethyl]-(2-p-tolylcarbamoyl-propyl)-phosphinic acid | 592.2 $(M - H)^-$ |
| I-21 | [(R)-1-(3-dipropylcarbamoyl-benzoylamino)-2-phenyl-ethyl]-((S)-2-p-tolylcarbamoyl-propyl)-phosphinic acid | 590.8 $(M - H)^-$ |
| I-22 | [(R)-1-(3-dipropylcarbamoyl-benzoylamino)-2-phenyl-ethyl]-((R)-2-p-tolylcarbamoyl-propyl)-phosphinic acid | 590.5 $(M - H)^-$ |

-continued

| No. | Compound of formula I | MS |
|---|---|---|
| I-23 | [1-(3-dipropylcarbamoyl-benzoylamino)-2-phenyl-ethyl]-[2-(3-ethoxy-phenylcarbamoyl)-ethyl]-phosphinic acid | 608.2 (M + H)$^+$ |
| I-24 | [1-(3-dipropylcarbamoyl-benzoylamino)-2-phenyl-ethyl]-[2-(3-trifluoromethyl-phenylcarbamoyl)-ethyl]-phosphinic acid | 632.3 (M + H)$^+$ |
| I-25 | [1-(3-dipropylcarbamoyl-benzoylamino)-2-phenyl-ethyl]-[2-(5-methyl-pyridin-2-ylcarbamoyl)-ethyl]-phosphinic acid | 579.2 (M + H)$^+$ |
| I-26 | [2-(4-tert-butyl-phenylcarbamoyl)-ethyl]-[1-(3-dipropylcarbamoyl-benzoylamino)-2-phenyl-ethyl]-phosphinic acid | 618.6 (M − H)$^-$ |
| I-27 | [2-(4-dimethylamino-phenylcarbamoyl)-ethyl]-[1-(3-dipropylcarbamoyl-benzoylamino)-2-phenyl-ethyl]-phosphinic acid | 607.2 (M + H)$^+$ |
| I-28 | [1-(3-dipropylcarbamoyl-benzoylamino)-2-phenyl-ethyl]-[2-(4-hydroxy-phenylcarbamoyl)-ethyl]-phosphinic acid | 580.2 (M + H)$^+$ |
| I-29 | 4-(3-{[1-(3-dipropylcarbamoyl-benzoylamino)-2-phenyl-ethyl]-hydroxy-phosphinoyl}-propionylamino)-benzoic acid methyl ester | 622.3 (M + H)$^+$ |
| I-30 | [2-(3,4-dimethoxy-phenylcarbamoyl)-ethyl]-[1-(3-dipropylcarbamoyl-benzoylamino)-2-phenyl-ethyl]-phosphinic acid | 624.2 (M + H)$^+$ |
| I-31 | [2-(3,5-dimethoxy-phenylcarbamoyl)-ethyl]-[1-(3-dipropylcarbamoyl-benzoylamino)-2-phenyl-ethyl]-phosphinic acid | 622.8 (M − H)$^-$ |
| I-32 | [1-(3-dipropylcarbamoyl-benzoylamino)-2-phenyl-ethyl]-[2-(3,4,5-tri-methoxy-phenylcarbamoyl)-ethyl]-phosphinic acid | 654.2 (M + H)$^+$ |
| I-33 | [1-(3-dipropylcarbamoyl-benzoylamino)-2-phenyl-ethyl]-[2-(1(S)-phenyl-ethylcarbamoyl)-ethyl]-phosphinic acid | 590.4 (M − H)$^-$ |
| I-34 | [2-(2-dimethylamino-ethylcarbamoyl)-ethyl]-[1-(3-dipropylcarbamoyl-benzoylamino)-2-phenyl-ethyl]-phosphinic acid | 559.2 (M + H)$^+$ |
| I-35 | [(R)-1-(3-dipropylcarbamoyl-benzoylamino)-2-phenyl-ethyl]-(2-iso-propylcarbamoyl-propyl)-phosphinic acid | 542.5 (M − H)$^-$ |
| I-36 | [(R)-1-(3-dipropylcarbamoyl-benzoylamino)-2-phenyl-ethyl]-(2-iso-butylcarbamoyl-propyl)-phosphinic acid | 556.5 (M − H)$^-$ |
| I-37 | [(R)-1-(3-dipropylcarbamoyl-benzoylamino)-2-phenyl-ethyl]-[2-(3-methyl-butylcarbamoyl)-propyl]-phosphinic acid | 570.5 (M − H)$^-$ |
| I-38 | [2-(3,3-dimethyl-butylcarbamoyl)-propyl]-[(R)-1-(3-dipropylcarbamoyl-benzoylamino)-2-phenyl-ethyl]-phosphinic acid | 584.5 (M − H)$^-$ |
| I-39 | [(R)-1-(3-dipropylcarbamoyl-benzoylamino)-2-phenyl-ethyl]-[2-(4,4,4-trifluoro-butylcarbamoyl)-propyl]-phosphinic acid | 610.4 (M − H)$^-$ |
| I-40 | [(R)-1-(3-dipropylcarbamoyl-benzoylamino)-2-phenyl-ethyl]-[2-(3,3,4,4-tetrafluoro-butylcarbamoyl)-propyl]-phosphinic acid | 628.5 (M − H)$^-$ |
| I-41 | [(R)-1-(3-dipropylcarbamoyl-benzoylamino)-2-phenyl-ethyl]-[2-(2,2,3,3,4,4,4-heptafluoro-butylcarbamoyl)-propyl]-phosphinic acid | 682.2 (M − H)$^-$ |
| I-42 | (2-cyclohexylcarbamoyl-propyl)-[(R)-1-(3-dipropylcarbamoyl-benzoylamino)-2-phenyl-ethyl]-phosphinic acid | 582.5 (M − H)$^-$ |
| I-43 | [2-(2-cyclohexyl-ethylcarbamoyl)-propyl]-[(R)-1-(3-dipropylcarbamoyl-benzoylamino)-2-phenyl-ethyl]-phosphinic acid | 610.4 (M − H)$^-$ |
| I-44 | [(R)-1-(3-dipropylcarbamoyl-benzoylamino)-2-phenyl-ethyl]-[2-(4-hydroxy-phenylcarbamoyl)-propyl]-phosphinic acid | 592.5 (M − H)$^-$ |
| I-45 | [(R)-1-(3-dipropylcarbamoyl-benzoylamino)-2-phenyl-ethyl]-[2-(4-methoxy-phenylcarbamoyl)-propyl]-phosphinic acid | 606.5 (M − H)$^-$ |
| I-46 | [(R)-1-(3-dipropylcarbamoyl-benzoylamino)-2-phenyl-ethyl]-[2-(pyridin-2-ylcarbamoyl)-propyl]-phosphinic acid | 577.6 (M − H)$^-$ |
| I-47 | [(R)-1-(3-dipropylcarbamoyl-benzoylamino)-2-phenyl-ethyl]-[2-(5-methyl-pyridin-2-ylcarbamoyl)-propyl]-phosphinic acid | 591.5 (M − H)$^-$ |
| I-48 | (2-benzylcarbamoyl-propyl)-[(R)-1-(3-dipropylcarbamoyl-benzoylamino)-2-phenyl-ethyl]-phosphinic acid | 590.5 (M − H)$^-$ |
| I-49 | {2-[(3,5-dimethyl-isoxazol-4-ylmethyl)-carbamoyl]-propyl}-[(R)-1-(3-dipropylcarbamoyl-benzoylamino)-2-phenyl-ethyl]-phosphinic acid | 609.5 (M − H)$^-$ |
| I-50 | [(R)-1-(3-dipropylcarbamoyl-benzoylamino)-2-phenyl-ethyl]-(2-phenethylcarbamoyl-propyl)-phosphinic acid | 604.7 (M − H)$^-$ |
| I-51 | [(R)-1-(3-dipropylcarbamoyl-benzoylamino)-2-phenyl-ethyl]-[2-(1-methyl-2-phenyl-ethylcarbamoyl)-propyl]-phosphinic acid | 618.6 (M − H)$^-$ |
| I-52 | {2-[2-(2,4-dimethyl-phenyl)-1-methyl-ethylcarbamoyl]-propyl}-[(R)-1-(3-dipropylcarbamoyl-benzoylamino)-2-phenyl-ethyl]-phosphinic acid | 646.5 (M − H)$^-$ |

By way of example NMR data [$^1$H-NMR (300 MHz, internal standard TMS, J values in Hz, CD$_3$OD)] are given for two compounds, i.e. compounds I-18 and I-37: Compound I-18: 7.77 (m, 1H), 7.67-7.47 (m, 5H), 7.40-7.07 (m, 8H), 4.80 (m, 1H), 3.60-2.95 (m, 7H), 2.55-2.27 (m, 1H), 2.05-1.80 (m, 1H), 1.80-1.45 (m, 4H), 1.42 and 1.39 (d each, J=6 each, ratio 3:2, 3H together), 1.04 (m, 3H), 0.70 (m, 3H). Compound I-37: 7.74 (m, 1H), 7.60 (s, 1H), 7.50 (m, 2H), 7.30-7.10 (m, 5H), 4.72 (m, 1H), 3.50-2.75 (m, 9H), 2.35-2.10 (m 1H), 1.90-1.30 (m 8H), 1.26 and 1.24 (d each, J=6 each, ratio 3:2, 3H together), 1.00 (m, 3H), 0.91 and 0.89 (d each, J=6 each, ratio 2:3, 6H together), 0.70 (m, 3H).

Example 3

Preparation of a Compound of Formula I Starting from Another Compound of Formula I A solution of 14 mg of 3-{[1-(3-dipropylcarbamoyl-benzoylamino)-2-phenyl-ethyl]-hydroxy-phosphinoylmethyl}-N-phenyl-succinamic acid methyl ester (compound I-17) in 1 ml of MeOH and 3 mg of NaOH was warmed to 45° for 3 h. The solution was evaporated, the residue partitioned between 1N aqueous hydrochloric acid and CH$_2$Cl$_2$, the organic layer was washed with water, dried and evaporated to give 11 mg of 3-{[1-(3-di-propylcarbamoyl-benzoylamino)-2-phenyl-ethyl]-hydroxy-phosphinoylmethyl}-N-phenyl-succinamic acid (compound 1-53).

| No. | Compound of formula I | MS |
|---|---|---|
| I-53 | 3-{[1-(3-dipropylcarbamoyl-benzoylamino)-2-phenyl-ethyl]-hydroxy-phosphinoylmethyl}-N-phenyl-succinamic acid | 620.3 (M − H)⁻ |

The compounds of the invention and pharmaceutically suitable salts thereof (hereinafter: Pharmaceutical Compounds) have pharmacological activity and are useful as pharmaceuticals. In particular, Pharmaceutical Compounds exhibit β-secretase inhibitory activity. Cellular screening methods for inhibitors of A-beta production, testing methods for the in vivo suppression of A-beta production, and assays with membranes or cellular extracts for the detection of secretase activity are known in the art and have been disclosed in numerous publications, including WO 98/22493, U.S. Pat. No. 5,703,129, U.S. Pat. No. 5,593,846 and GB 2,395,124; all hereby incorporated by reference. Beta-secretase has been described in several publications including EP 855,444, WO 00/17,369, WO 00/58,479, WO 00/47,618, WO 01/00,663 and WO 01/00,665.

For example, inhibition of β-secretase of the Pharmaceutical Compounds may be demonstrated by their ability, e.g., to inhibit the cleavage of a fluorescent peptide substrate (e.g. in an assay like e.g. the FRET Assay as described inter alia by Grueninger-Leitch et al.) or to displace, e.g., a peptidic β-secretase inhibitor at the active binding site of β-secretase, e.g. as demonstrated in accordance with the following test method.

Competitive Radioligand Binding Assay (RLBA)

96 well microplates (Optiplate Packard) are coated with purified BACE protein (see e.g. GB 2,385,124: Examples 1 and 2) using a concentration of 1 μg/ml in 30 mM sodium citrate buffer adjusted to pH 5.5. The coating is achieved by incubation of 100 μl/well for 1-3 days at 4° C. The plate is then washed with 2×300 μl/well of 10 mM citrate pH 4.1. To each well 100 μl binding buffer (30 mM citrate, 100 mM NaCl, 0.1% BSA, pH 4.1) is dispensed. The test compound is added in 5 μl from a DMSO stock solution or appropriate dilutions. To this the tracer (tritiated Compound A, see e.g. GB 2,385,124: Example 4) is added in 10 l/well from a 10 μCi/ml stock solution in binding buffer. After incubation for 1.5-2 hours in a humid chamber at ambient temperature the plate is washed with 2×300 μl/well water and flipped on a dry towel. Following the addition of 50 μl/well Micro-Scint20 (Packard) the plate is sealed and vibrated for 5 seconds. The bound radioactivity is counted on a Topcount (Packard). Total binding is typically between 2000 and 10000 cpm/well depending mainly on the purity and concentration of the BACE protein. Non-specific binding as assessed by competition with >1 μM peptidic inhibitor (Bachem # H-4848) is typically between 30 and 300 cpm/well. The IC-50 values are calculated by Microsoft Excel FIT.

The preferred compounds show an $IC_{50}$<1.0 μM. In the list below some exemplary data for the β-secretase inhibition are given:

| Example No. | $IC_{50}$ in vitro [μM] |
|---|---|
| I-5 | 0.05 |
| I-14 | 0.20 |
| I-18 | 0.01 |
| I-37 | 0.04 |
| I-42 | 0.02 |

Pharmaceutical Compounds are accordingly useful as β-secretase inhibitors, e.g. in the treatment of diseases and conditions in which β-secretase activity plays a role or is implicated. Such conditions include in particular Alzheimer's disease and Cerebral Amyloid Angiopathy.

Beta-secretase inhibitors can be further optimized for their ability to inhibit the secretion of A-beta in cell culture systems which are well known in the art. For example, the production of A-beta can be measured by immunoassay in cell culture supernatant of HEK293 cells which overexpress by transfection the amyloid precursor protein (APP). The A-beta production can also be measured in supernatant human neuroblastoma cell lines which express the endogenous APP. In addition, beta-secretase inhibitors can be optimized for efficacy in transgenic mouse models of Alzheimer's disease which generate A-beta containing Alzheimer-like plaques in the CNS of the affected mice. Finally, beta-secretase inhibitors are expected to reduce the A-beta concentration in the brain and in cerebrospinal fluid of patients suffering from Alzheimer's disease and also in healthy individuals which have not yet developed A-beta plaques.

Biochemical and immunological studies revealed that the dominant proteinaceous component of the amyloid plaque occurring in the cerebral cortex of individuals effected by Alzheimer's disease (AD) is an approximately 4.2 kilodalton (kD) protein of about 39 to 43 amino acids. This protein was designated A-beta-amyloid peptide, and sometimes beta/A4; referred to herein as A-beta. In addition to deposition of A-beta in amyloid plaques, A-beta is also found in the walls of meningeal and parenchymal arterioles, small arteries, capillaries, and sometimes, venules. Since there are strong indications that A-beta depositions are causally related to AD, it would be desirable to inhibit the formation of A-beta in vivo thus preventing and reducing neurological degeneration, by controlling the formation of amyloid plaques, reducing neurotoxicity and, generally, mediating the pathology associated with A-beta production beta appears to be an internal polypeptide derived from a type 1 integral membrane protein, termed beta amyloid precursor protein (APP). APP is normally produced by many cells both in vivo and in cultured cells, derived from various animals and humans. A-beta is derived from cleavage of APP by an enzyme (protease) system(s), collectively termed secretases, including beta-secretase(s), generating the N-terminus of A-beta.

In another embodiment, the present invention provides pharmaceutical compositions containing compounds of the invention or pharmaceutically acceptable salts thereof and a pharmaceutically acceptable carrier. Such pharmaceutical compositions can be in the form of tablets, coated tablets, dragees, hard and soft gelatine capsules, solutions, emulsions or suspensions. The pharmaceutical compositions also can be in the form of suppositories or injectable solutions.

The pharmaceutical compositions of the invention, in addition to one or more Pharmaceutical Compounds of the invention, contain a pharmaceutically acceptable carrier. Suitable pharmaceutically acceptable carriers include pharmaceutically inert, inorganic or organic carriers for the production of pharmaceutical preparations. Lactose, corn starch or derivatives thereof, talc, stearic acids or its salts and the like can be used, e.g., as such carriers for tablets, coated tablets, dragees and hard gelatine capsules. Suitable carriers for soft gelatine capsules are, e.g., vegetable oils, waxes, fats, semi-solid and liquid polyols and the like. Depending on the nature of the active substance no carriers are, however, usually required in the case of soft gelatine capsules. Suitable carriers for the production of solutions and syrups are, e.g., water, polyols, glycerol, vegetable oil and the like. Suitable carriers for suppositories are, e.g., natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more Pharmaceutical Compound and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatine capsules, solutions, emulsions, or suspensions. The pharmaceutical compositions also can be administered rectally, for example, in the form of suppositories, or parenterally, for example, in the form of injectable solutions.

Compounds of the invention are β-secretase inhibitors. Therefore, the present invention also provides a method for treating diseases that are mediated by β-secretase. Such methods include administering a therapeutically effective amount of a compound of the invention, for example, a compound of formula I, or a pharmaceutically acceptable salt thereof, to a patient in need of such treatment. In a preferred embodiment, the invention provides a method for the treatment of Alzheimer's disease.

The dosage at which the compound can be administered can vary within wide limits and will, of course, have to be adjusted to the individual requirements in each particular case. In the case of oral administration the dosage for adults can vary from about 0.01 mg to about 1000 mg per day of a Pharmaceutical Compound. The daily dosage may be administered as single dose or in divided doses and, in addition, the upper limit can also be exceeded when this is found to be indicated.

Tablet Formulation (Wet Granulation)

|   |   | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |

-continued

Tablet Formulation (Wet Granulation)

|   |   | mg/tablet | | | |
|---|---|---|---|---|---|
| Item | Ingredients | 5 mg | 25 mg | 100 mg | 500 mg |
| 5. | Magnesium Stearate | 1 | 1 | 1 | 1 |
|   | Total | 167 | 167 | 167 | 831 |

Mix items 1, 2, 3 and 4 and granulate with purified water. Dry the granules at 50° C. Pass the granules through suitable milling equipment. Add item 5 and mix for three minutes; compress on a suitable press.

Capsule Formulation

|   |   | mg/capsule | | | |
|---|---|---|---|---|---|
| Item | Ingredients | 5 mg | 25 mg | 100 mg | 500 mg |
|   | Compound of formula I | 5 | 25 | 100 | 500 |
|   | Hydrous Lactose | 159 | 123 | 148 | — |
|   | Corn Starch | 25 | 35 | 40 | 70 |
|   | Talc | 10 | 15 | 10 | 25 |
|   | Magnesium Stearate | 1 | 1 | 2 | 5 |
|   | Total | 200 | 200 | 300 | 600 |

Mix items 1, 2 and 3 in a suitable mixer for 30 minutes. Add items 4 and 5 and mix for 3 minutes. Fill into a suitable capsule.

What is claimed is:

1. A compound of formula I

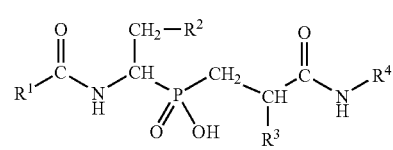

(I)

wherein $R^1$ is a group of formula (a)

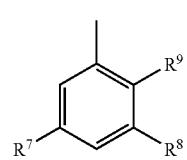

(a)

$R^7$ is hydrogen, $(C_1-C_5)$-alkyl or $O—(C_1-C_4)$-alkyl;

$R^8$ is OH, pyrrolidonyl or $—C(O)NR^5R^6$ wherein $R^5$ is hydrogen or $(C_1-C_5)$-alkyl and $R^6$ is $(C_1-C_5)$-alkyl or $(C_1-C_5)$-alkyl substituted by phenyl; and $R^9$ is hydrogen or $(C_1-C_5)$-alkyl; or $R^1$ is indolyl substituted by $(C_1-C_5)$-alkyl, or quinolinyl;

$R^2$ is $(C_1-C_5)$-alkyl or phenyl;

$R^3$ is hydrogen, $(C_1-C_5)$-alkyl, $O—(C_1-C_5)$-alkyl or phenyl;

$R^4$ is $(C_1-C_6)$-alkyl, $(C_3-C_6)$-cycloalkyl, phenyl, pyridyl, or indolyl;

or a pharmaceutically acceptable salt thereof.

2. The compound of formula I according to claim 1 wherein
R$^1$ is a group of formula (a)

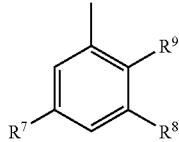

R$^7$ is hydrogen or (C$_1$-C$_5$)-alkyl;
R$^8$ is —C(O)NR$^5$R$^6$ wherein R$^5$ is hydrogen or (C$_1$-C$_5$)-alkyl and R$^6$ is (C$_1$-C$_5$)-alkyl or (C$_1$-C$_5$)-alkyl substituted by phenyl; and
R$^9$ is hydrogen.

3. The compound of formula I according to claim 1 wherein
R$^1$ is a group of formula (a)

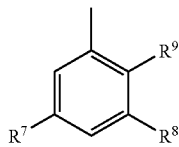

R$^7$ is hydrogen or (C$_1$-C$_5$)-alkyl;
R$^8$ is —C(O)NR$^5$R$^6$ wherein R$^5$ is (C$_1$-C$_5$)-alkyl and R$^6$ is (C$_1$-C$_5$)-alkyl or CH$_2$-phenyl; and
R$^9$ is hydrogen.

4. The compound of formula I according to claim 1 wherein
R$^1$ is a group of formula (a)

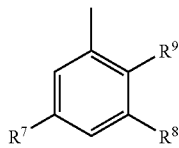

R$^7$ is hydrogen or O—(C$_1$-C$_4$)-alkyl;
R$^8$ is OH or pyrrolidonyl; and
R$^9$ is hydrogen or (C$_1$-C$_5$)-alkyl.

5. The compound of formula I according to claim 1 wherein R$^1$ is indolyl substituted by (C$_1$-C$_5$)-alkyl or quinolinyl.

6. The compound of formula I according to claim 5 wherein R$^1$ is 1-butyl-indolyl-6-yl or quinoline-2-yl.

7. The compound of formula I according to claim 1 wherein R$^2$ is phenyl which is unsubstituted or substituted with fluorine.

8. The compound of formula I according to claim 1 wherein R$^2$ is (C$_1$-C$_5$)-alkyl which is unsubstituted or substituted with S-(C$_1$-C$_5$)-alkyl.

9. The compound of formula I according to claim 1 wherein R$^3$ is hydrogen, (C$_1$-C$_5$)-alkyl or phenyl.

10. The compound of formula I according to claim 1 wherein R$^3$ is hydrogen;
(C$_1$-C$_5$)-alkyl which is unsubstituted or substituted by phenyl, COOH, or COOCH$_3$; or phenyl.

11. The compound of formula I according to claim 10 wherein R$^3$ is hydrogen, methyl, ethyl, isopropyl, phenyl, CH$_2$-phenyl, CH$_2$COOH or CH$_2$COOCH$_3$.

12. The compound of formula I according to claim 11 wherein R$^3$ is methyl.

13. The compound of formula I according to claim 1 wherein R$^4$ is unsubstituted (C$_1$-C$_6$)-alkyl;
(C$_1$-C$_6$)-alkyl substituted by one or more substituents selected from halogen, N[(C$_1$-C$_6$)-alkyl]$_2$, (C$_3$-C$_6$)-cycloalkyl, unsubstituted phenyl, phenyl substituted by one or more (C$_1$-C$_5$)-alkyl, and isoxazolyl substituted by one or more (C$_1$-C$_5$)-alkyl;
cyclohexyl;
unsubstituted phenyl;
phenyl substituted by OH, N[(C$_1$-C$_6$)-alkyl]$_2$, unsubstituted (C$_1$-C$_5$)-alkyl, (C$_1$-C$_6$)-alkyl substituted by halogen; O—(C$_1$-C$_4$)-alkyl or COO(C$_1$-C$_5$)-alkyl;
unsubstituted pyridyl; or
pyridyl substituted by methyl.

14. The compound of formula I according to claim 13 wherein R$^4$ is unsubstituted phenyl.

15. The compound of formula I according to claim 13 wherein R$^4$ is phenyl substituted by OH, N(CH$_3$)$_2$, methyl, isobutyl, trifluoromethyl, methoxy, ethoxy, or COOCH$_3$.

16. The compound of formula I according to claim 13 wherein R$^4$ is unsubstituted (C$_1$-C$_5$)-alkyl.

17. The compound of formula I according to claim 13 wherein R$^4$ is (C$_1$-C$_5$)-alkyl substituted by one or more substituents selected from halogen, N[(C$_1$-C$_6$)-alkyl]$_2$, (C$_3$-C$_6$)-cycloalkyl, unsubstituted phenyl, phenyl substituted by one or more (C$_1$-C$_5$)-alkyl, and isoxazolyl substituted by one or more (C$_1$-C$_5$)-alkyl.

18. The compound of formula I according to claim 17 wherein R$^4$ is methyl substituted by phenyl or by isoxazol substituted by methyl.

19. The compound of formula I according to claim 17 wherein R$^4$ is ethyl substituted by cyclohexyl, phenyl, or N(CH$_3$)$_2$.

20. The compound of formula I according to claim 17 wherein R$^4$ is propyl substituted by phenyl or dimethylphenyl.

21. The compound of formula I according to claim 17 wherein R$^4$ is butyl substituted by fluorine.

22. The compound of formula I according to claim 13 wherein R$^4$ is cyclohexyl.

23. The compound of formula I according to claim 13 wherein R$^4$ is pyridyl which is unsubstituted or substituted with methyl.

24. The compound of formula I according to claim 1 wherein
R$^1$ is a group of formula (a)

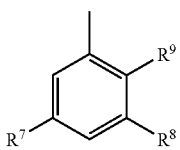

wherein
R$^7$ is hydrogen;
R$^8$ is —C(O)NR$^5$R$^6$ wherein R$^5$ is hydrogen or (C$_1$-C$_5$)-alkyl and R$^6$ is (C$_1$-C$_5$)-alkyl or (C$_1$-C$_5$)-alkyl substituted by phenyl;
R$^9$ is hydrogen;

R² is phenyl;
R³ is hydrogen, (C₁-C₅)-alkyl, or phenyl; and
R⁴ is unsubstituted (C₁-C₆)-alkyl or (C₁-C₆)-alkyl substituted by one or more substituents selected from halogen, N[(C₁-C₆)-alkyl]₂, (C₃-C₆)-cycloalkyl, unsubstituted phenyl, phenyl substituted by one or more (C₁-C₅)-alkyl, and isoxazolyl substituted by one or more (C₁-C₅)-alkyl;
cyclohexyl;
unsubstituted phenyl or phenyl substituted by OH, N[(C₁-C₆)-alkyl]₂, unsubstituted (C₁-C₆)-alkyl, (C₁-C₆)-alkyl substituted by halogen; O—(C₁-C₄)-alkyl or COO(C₁-C₅)-alkyl; or unsubstituted pyridyl or pyridyl substituted by methyl.

25. The compound of formula I according to claim 1 wherein
R¹ is a group of formula (a)

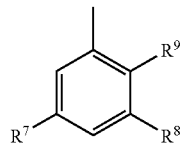

wherein
R⁷ is hydrogen, (C₁-C₅)-alkyl or O—(C₁-C₄)-alkyl;
R⁸ is OH, pyrrolidonyl or —C(O)NR⁵R⁶ wherein R⁵ is hydrogen or (C₁-C₅)-alkyl and R⁶ is (C₁-C₅)-alkyl or (C₁-C₅)-alkyl substituted by phenyl; and
R⁹ is hydrogen or (C₁-C₅)-alkyl;
R² is unsubstituted phenyl; phenyl substituted by fluorine; unsubstituted (C₁-C₅)-alkyl; or (C₁-C₅)-alkyl substituted by S—(C₁-C₅)-alkyl;
R³ is hydrogen, (C₁-C₅)-alkyl; or phenyl; and
R⁴ is unsubstituted (C₁-C₆)-alkyl; (C₁-C₆)-alkyl substituted by one or more substituents selected from halogen, N[(C₁-C₆)-alkyl]₂, (C₃-C₆)-cycloalkyl, unsubstituted phenyl, phenyl substituted by one or more (C₁-C₅)-alkyl, and isoxazolyl substituted by one or more (C₁-C₅)-alkyl;
cyclohexyl;
unsubstituted phenyl;
phenyl substituted by OH, N[(C₁-C₆)-alkyl]₂, unsubstituted (C₁-C₆)-alkyl, (C₁-C₆)-alkyl substituted by halogen; O—(C₁-C₄)-alkyl or COO(C₁-C₅)-alkyl;
unsubstituted pyridyl; or
pyridyl substituted by methyl.

26. The compound of formula I according to claim 1 wherein
R¹ is indolyl substituted by (C₁-C₅)-alkyl or is quinolinyl;
R² is phenyl;
R³ is (C₁-C₅)-alkyl; and
R⁴ is phenyl.

27. The compound of formula I according to claim 1 selected from
{(R)-1-[3-(methyl-propyl-carbamoyl)-benzoylamino]-2-phenyl-ethyl}-(2-phenylcarbamoyl-propyl)-phosphinic acid,
{(R)-1-[3-(methyl-pentyl-carbamoyl)-benzoylamino]-2-phenyl-ethyl}-(2-phenylcarbamoyl-propyl)-phosphinic acid,
[(R)-1-(3-dipentylcarbamoyl-benzoylamino)-2-phenyl-ethyl]-(2-phenylcarbamoyl-propyl)-phosphinic acid,
[(R)-1-(3-dipropylcarbamoyl-5-methyl-benzoylamino)-2-phenyl-ethyl]-(2-phenylcarbamoyl-propyl)-phosphinic acid,
{(R)-1-[3-(2-oxo-pyrrolidin-1-yl)-5-propoxy-benzoylamino]-2-phenyl-ethyl}-(2-phenyl-carbamoyl-propyl)-phosphinic acid,
{(R)-1-[(1butyl-1H-indole-6-carbonyl)-amino]-2-phenyl-ethyl}-(2-phenylcarbonyl-propyl)-phosphinic acid,
[1-(3-dipropylcarbamoyl-benzoylamino)-2-phenyl-ethyl]-(2-p-tolylcarbamoyl-butyl)-phosphinic acid,
[1-(3-dipropylcarbamoyl-benzoylamino)-2-phenyl-ethyl]-(3-methyl-2-p-tolylcarbamoyl-butyl)-phosphinic acid, and
[1-(3-dipropylcarbamoyl-benzoylamino)-2-phenyl-ethyl]-(2-phenyl-2-p-tolylcarbamoyl-ethyl)-phosphinic acid.

28. The compound of formula I according to claim 1 selected from
[(R)-1-(3-dipropylcarbamoyl-benzoylamino)-2-phenyl-ethyl]-(2-phenylcarbamoyl-propyl)-phosphinic acid,
[(R)-1-(3-dipropylcarbamoyl-benzoylamino)-2-phenyl-ethyl]-((S)-2-phenylcarbamoyl-propyl)-phosphinic acid,
[(R)-1-(3-dipropylcarbamoyl-benzoylamino)-2-phenyl-ethyl]-(2-p-tolylcarbamoyl-propyl)-phosphinic acid,
[(R)-1-(3-dipropylcarbamoyl-benzoylamino)-2-phenyl-ethyl]-((S)-2-p-tolylcarbamoyl-propyl)-phosphinic acid,
[(R)-1-(3-dipropylcarbamoyl-benzoylamino)-2-phenyl-ethyl]-((R)-2-p-tolylcarbamoyl-propyl)-phosphinic acid,
[(R)-1-(3-dipropylcarbamoyl-benzoylamino)-2-phenyl-ethyl]-(2-isobutylcarbamoyl-propyl)-phosphinic acid,
[(R)-1-(3-dipropylcarbamoyl-benzoylamino)-2-phenyl-ethyl]-[2-(3-methyl-butylcarbamoyl)-propyl]-phosphinic acid,
[2-(3,3-dimethyl-butylcarbamoyl)-propyl]-[(R)-1-(3-dipropylcarbamoyl-benzoylamino)-2-phenyl-ethyl]-phosphinic acid, and
[(R)-1-(3-dipropylcarbamoyl-benzoylamino)-2-phenyl-ethyl]-[2-(4,4,4-trifluoro-butyl-carbamoyl)-propyl]-phosphinic acid.

29. The compound of formula I according to claim 1 selected from
[(R)-1-(3-dipropylcarbamoyl-benzoylamino)-2-phenyl-ethyl]-[2-(3,3,4,4-tetrafluoro- butylcarbamoyl)-propyl]-phosphinic acid,
[(R)-1-(3-dipropylcarbamoyl-benzoylamino)-2-phenyl-ethyl]-[2-(2,2,3,3,4,4,4-heptafluoro- butylcarbamoyl)-propyl]-phosphinic acid,
(2-cyclohexylcarbamoyl-propyl)-[(R)-1-(3-dipropylcarbamoyl-benzoylamino)-2-phenyl-ethyl]-phosphinic acid,
[2-(2-cyclohexyl-ethylcarbamoyl)-propyl]-[(R)-1-(3-dipropylcarbamoyl-benzoylamino)-2-phenyl-ethyl]-phosphinic acid,
[(R)-1-(3-dipropylcarbamoyl-benzoylamino)-2-phenyl-ethyl]-[2-(4-hydroxy-phenylcarbamoyl)-propyl]-phosphinic acid,
[(R)-1-(3-dipropylcarbamoyl-benzoylamino)-2-phenyl-ethyl]-[2-(4-methoxy-phenylcarbamoyl)-propyl]-phosphinic acid,
[(R)-1-(3-dipropylcarbamoyl-benzoylamino)-2-phenyl-ethyl]-[2-(pyridin-2-ylcarbamoyl)-propyl]-phosphinic acid,

[(R)-1-(3-dipropylcarbamoyl-benzoylamino)-2-phenyl-ethyl]-[2-(5-methyl-pyridin-2-ylcarbamoyl)-propyl]-phosphinic acid and
(2-benzylcarbamoyl-propyl)-[(R)-1-(3-dipropylcarbamoyl-benzoylamino)-2-phenyl-ethyl]-phosphinic acid.

30. A composition comprising a compound of formula I

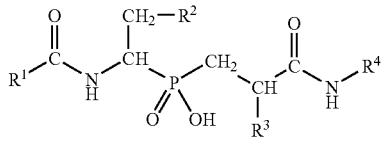

wherein
R¹ is

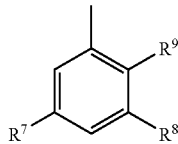

$R^7$ is hydrogen, $(C_1-C_5)$-alkyl or $O-(C_1-C_4)$-alkyl;
$R^8$ is OH, pyrrolidonyl or $-C(O)NR^5R^6$ wherein $R^5$ is hydrogen or $(C_1-C_5)$-alkyl and $R^6$ is $(C_1-C_5)$-alkyl or $(C_1-C_5)$-alkyl substituted by phenyl; and
$R^9$ is hydrogen or $(C_1C_5)$-alkyl; or
$R^1$ is indolyl substituted by $(C_1-C_5)$-alkyl, or quinolinyl;
$R^2$ is $(C_1-C_5)$-alkyl or phenyl;
$R^3$ is hydrogen, $(C_1-C_5)$-alkyl, $O-(C_1-C_5)$-alkyl or phenyl;
$R^4$ is $(C_1-C_6)$-alkyl, $(C_3-C_6)$-cycloalkyl, phenyl, pyridyl, or indolyl;
or a pharmaceutically acceptable salt thereof and a pharmaceutically acceptable carrier.

31. A process for the preparation of a compound of formula I

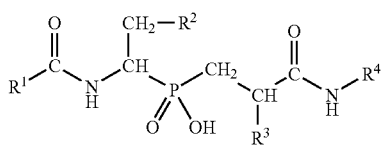

wherein
R¹ is

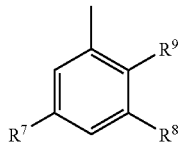

$R^7$ is hydrogen, $(C_1-C_5)$-alkyl or $O-(C_1-C_4)$-alkyl;
$R^8$ is OH, pyrrolidonyl or $-C(O)NR^5R^6$ wherein $R^5$ is hydrogen or $(C_1-C^5)$-alkyl and $R^6$ is $(C_1-C_5)$-alkyl or $(C_1-C_5)$-alkyl substituted by phenyl; and
$R^9$ is hydrogen or $(C_1-C_5)$-alkyl; or
$R^1$ is indolyl substituted by $(C_1-C_5)$-alkyl, or quinolinyl;
$R^2$ is $(C_1-C_5)$-alkyl or phenyl;
$R^3$ is hydrogen, $(C_1-C_5)$-alkyl, $O-(C_1-C_5)$-alkyl or phenyl;
$R^4$ is $(C_1-C_6)$-alkyl, $(C_3-C_6)$-cycloalkyl, phenyl, pyridyl, or indolyl;
comprising reacting a compound of formula II

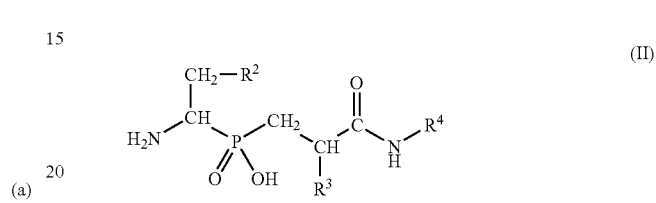

wherein
$R^2$ is $(C_1-C_5)$-alkyl or phenyl;
$R^3$ is hydrogen, $(C_1-C_5)$-alkyl, $O-(C_1-C_5)$-alkyl or phenyl; and
$R^4$ is $(C_1-C_6)$-alkyl, $(C_3-C_6)$-cycloalkyl, phenyl, pyridyl, or indolyl;
with a compound of formula III $$R^1\text{-COR}^{10} \qquad (III)$$

wherein
R¹ is

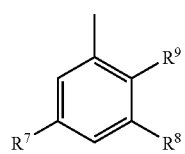

$R^7$ is hydrogen, $(C_1-C_5)$-alkyl or $O-(C_1-C_4)$-alkyl;
$R^8$ is OH, pyrrolidonyl or $-C(O)NR^5R^6$ wherein $R^5$ is hydrogen or $(C_1-C_5)$-alkyl and $R^6$ is $(C_1-C_5)$-alkyl or $(C_1-C_5)$-alkyl substituted by phenyl; and
$R^9$ is hydrogen or $(C_1-C_5)$-alkyl; or
$R^1$ is indolyl substituted by $(C_1-C_5)$-alkyl, or quinolinyl; and
$R^{10}$ is halogen or OH.

32. A process for the preparation of a compound of formula I

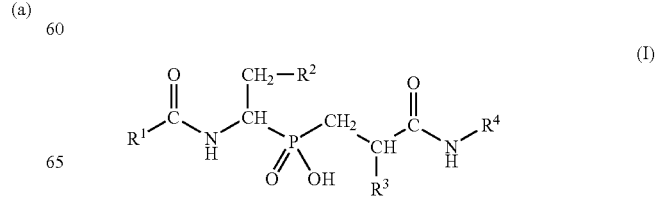

wherein
R¹ is

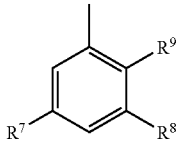
(a)

R⁷ is hydrogen, $(C_1-C_5)$-alkyl or O—$(C_1-C_4)$-alkyl;
R⁸ is OH, pyrrolidonyl or —C(O)NR⁵R⁶ wherein R⁵ is hydrogen or $(C_1-C_5)$-alkyl and R⁶ is $(C_1-C_5)$-alkyl or $(C_1-C_5)$-alkyl substituted by phenyl; and
R⁹ is hydrogen or $(C_1-C_5)$-alkyl; or
R¹ is indolyl substituted by $(C_1-C_5)$-alkyl, or quinolinyl;
R² is $(C_1-C_5)$-alkyl or phenyl;
R³ is hydrogen, $(C_1-C_5)$-alkyl, O—$(C_1-C_5)$-alkyl or phenyl;
R⁴ is $(C_1-C_6)$-alkyl, $(C_3-C_6)$-cycloalkyl, phenyl, pyridyl, or indolyl;
comprising reacting a compound of formula XI

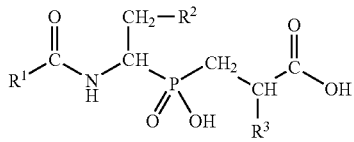
(XI)

wherein
R¹ is

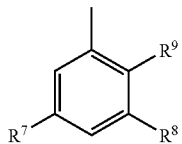
(a)

R⁷ is hydrogen, $(C_1-C_5)$-alkyl or O—$(C_1-C_4)$-alkyl;
R⁸ is OH, pyrrolidonyl or —C(O)NR⁵R⁶ wherein R⁵ is hydrogen or $(C_1-C_5)$-alkyl and R⁶ is $(C_1-C_5)$-alkyl substituted by phenyl; and
R⁹ is hydrogen or $(C_1-C_5)$-alkyl; or
R¹ is indolyl substituted by $(C_1-C_5)$-alkyl, or quinolinyl;
R² is $(C_1-C_5)$-alkyl or phenyl;
R³ is hydrogen, $(C_1-C_5)$-alkyl, O—$(C_1-C_5)$-alkoxy or phenyl;
with a compound of formula XII $H_2N—R^4$ (XII)

wherein
R⁴ is $(C_1-C_6)$-alkyl, $(C_3-C_6)$-cycloalkyl, phenyl, pyridyl or indolyl.

* * * * *